(12) United States Patent
Krumme et al.

(10) Patent No.: US 10,806,703 B2
(45) Date of Patent: Oct. 20, 2020

(54) TRANSMUCOSAL ADMINISTRATION SYSTEM FOR A PHARMACEUTICAL DRUG

(75) Inventors: Markus Krumme, Neuwied (DE); Keith Jensen, Clifton, NJ (US); Judith Dubach-Powell, Oberwil (CH); Rudolf Hausmann, Basel (CH)

(73) Assignees: LTS Lohmann Therapie-System AG, Andernach (DE); Santhera Pharmaceuticals (Schweitz) AG, Pratteln (CH)

( * ) Notice: Subject to any disclaimer, the term of this patent is extended or adjusted under 35 U.S.C. 154(b) by 454 days.

(21) Appl. No.: 13/354,714

(22) Filed: Jan. 20, 2012

(65) Prior Publication Data

US 2013/0189343 A1 Jul. 25, 2013

(51) Int. Cl.

| *A61K 9/70* | (2006.01) |
| *A61K 31/122* | (2006.01) |
| *A61K 9/00* | (2006.01) |
| *A61K 47/38* | (2006.01) |
| *A61K 47/32* | (2006.01) |

(52) U.S. Cl.
CPC ............ *A61K 9/7007* (2013.01); *A61K 9/006* (2013.01); *A61K 9/0056* (2013.01); *A61K 31/122* (2013.01); *A61K 47/32* (2013.01); *A61K 47/38* (2013.01)

(58) Field of Classification Search
None
See application file for complete search history.

(56) References Cited

U.S. PATENT DOCUMENTS

| 2002/0147201 A1* | 10/2002 | Chen et al. ............... 514/252.15 |
| 2006/0182786 A1* | 8/2006 | Rademacher ................. 424/443 |
| 2006/0222708 A1* | 10/2006 | Krumme et al. ............. 424/468 |
| 2009/0208425 A1* | 8/2009 | Dubach-Powell et al. ..... 424/48 |

FOREIGN PATENT DOCUMENTS

| CN | 1812765 A | 8/2006 |
| CN | 101541317 A | 9/2009 |
| EP | 2 108 366 A1 | 10/2009 |
| EP | 2108366 A1 | 10/2009 |
| JP | 2001-504106 A | 3/2001 |
| JP | 2001-506612 A | 5/2001 |
| JP | 2001-508037 A | 6/2001 |
| JP | 2004-43450 A | 2/2004 |
| JP | 2011-516513 A | 5/2011 |
| WO | WO 2005/019232 A1 | 3/2005 |
| WO | 2008019769 A1 | 2/2008 |
| WO | WO 2008/019769 A1 | 2/2008 |

OTHER PUBLICATIONS

Joshi, Jalay T., "A Review on Micronization Techniques," Journal of Pharmaceutical Science and Technology, vol. 3, No. 7, pp. 651-681 (2011).*
A. Mordente, et al. *Chem. Res. Toxicol.* 11 (1998), pp. 54-63.
M. Suno, et al. *Arch. Gerontol. Geriatr.* 8 (1989), pp. 307-311.
K. Yamada, et al. *Behavioural Brain Research* 83 (1997), pp. 117-122.
A. O. Hausse, et al. *Heart* 87 (2002), pp. 346-349.
N.A. Di Prospero, et al. *Lancet Neurol* 6 (2007) pp. 878-886.
L. J. Thal, et al, *Neurology* 61 (2003), pp. 1498-1502.
R. Artuch, et al. *Journal of Neuroscience Methods* 115 (2002), pp. 63-66.
European Search Report, Application No. 18212173.

* cited by examiner

*Primary Examiner* — Dennis J Parad
(74) *Attorney, Agent, or Firm* — ProPat, LLC; Cathy R. Moore

(57) ABSTRACT

The present invention relates to a transmucosal administration system to administer quinones, benzoquinones, and especially 1,4-benzoquinones, via the oromucosal route.

39 Claims, 1 Drawing Sheet

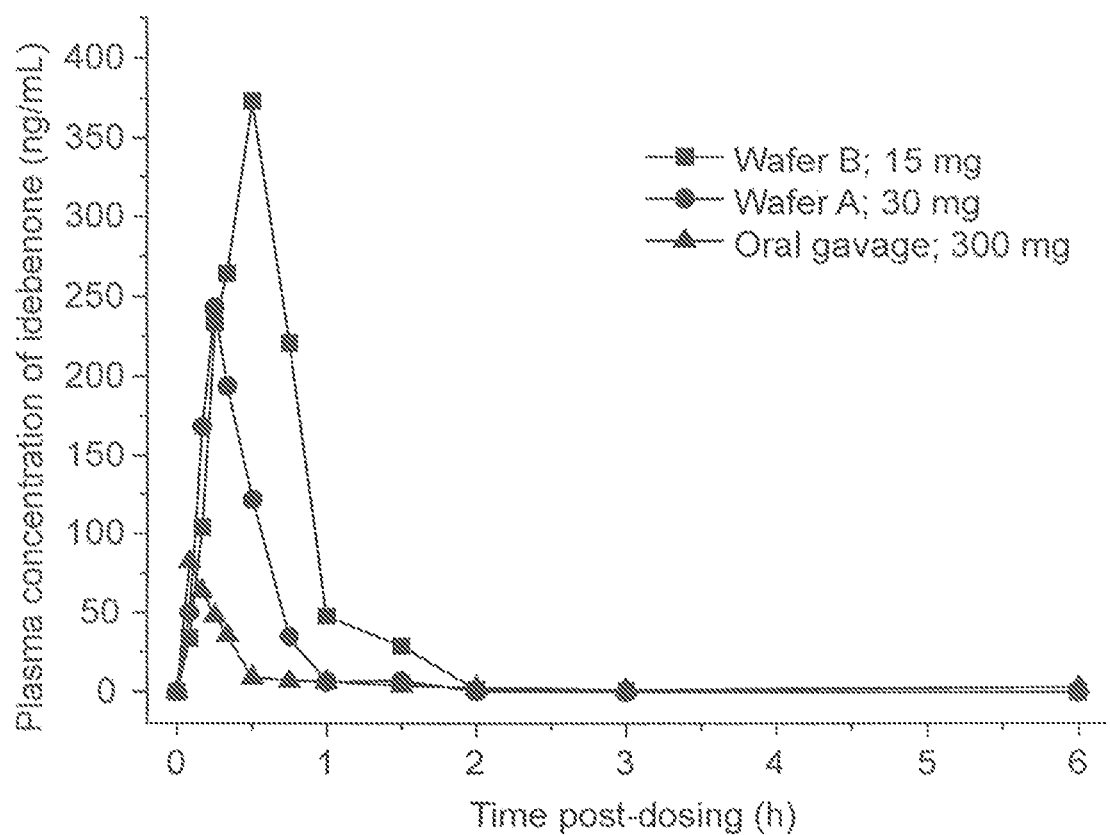

TRANSMUCOSAL ADMINISTRATION SYSTEM FOR A PHARMACEUTICAL DRUG

FIELD OF THE INVENTION

The present invention relates to a transmucosal administration system to administer quinones, benzoquinones, and especially 1,4-benzoquinones via the oromucosal route to a patient. Specifically, the present invention relates to a transmucosal administration system to administer 2,3-dimethoxy-5-metriyl-6-(10-hydroxydecyl)-1,4-benzoquinone (idebenone) and its analogues via a film formulation (oral wafer).

BACKGROUND OF THE INVENTION

Idebenone is a synthetic analogue of coenzyme Q10 (CoQ10), a vital cell membrane antioxidant and essential constituent of the adenosine-triphosphate (ATP) producing mitochondrial electron transport chain (ETC). Up to now, idebenone has been used in a variety of medical applications. Similar to coenzyme Q10, idebenone undergoes reduction/oxidation cycles in living organisms and reduced idebenone is an antioxidant and radical scavenger (A. Mordente, G. E. Martorana, G. Minotti, B. Giardina, *Chem. Res. Toxicol.* 11 (1998), 54-63). It is known that idebenone protects cell membranes and mitochondria from oxidative damage because of its ability to inhibit lipid peroxidation (M. Suno, M. Shibota, A. Nagaoka, *Arch. Gerontol. Geriatr.* 8 (1989), 307-311). Idebenone also interacts with the ETC, preserving ATP formation in ischemic states. It has been shown that the compound stimulates nerve growth factor, a characteristic that could be important for the treatment of Alzheimer's and other neurodegenerative diseases (K. Yamada, A. Nitta, T. Hasegawa, K. Fuji, M. Hiramatsu, T. Kameyama, Y. Furukawa, K. Hayashi, T. Nabeshima, *Behav. Brain Res.* 83 (1997), 117-122). The compound has also been suggested for the treatment of Friedreich's Ataxia and other mitochondrial and neuromuscular diseases (A. O. Hausse, Y. Aggoun, D. Bonnet, D. Sidi, A. Munnich, A. Rotig, P. Rustin, *Heart* 87 (2002), 346-349; Di Prospero N. A., Baker A., Jeffries N, Fischbeck K. H. *Lancet Neurol* 6 (2007) 878-886).

As a lipophilic compound idebenone is well absorbed in the gastrointestinal tract after conventional oral administration, which is the normal route for administering said compound. Dosage forms such as tablets or capsules have been used in clinical trials and as marketed product. In the course of our investigations on the pharmacological profile of idebenone, we discovered that the compound, after being absorbed in the gut, is metabolized very quickly during its first passage through the liver ("first-pass-effect"). Experiments showed that more than 98% of the idebenone is metabolized during its first passage through the liver. Hepatic metabolism of idebenone results in side chain oxidation, reduction of the quinone ring, sulphate and glucuronide conjugation and subsequent renal excretion. The high liver metabolism greatly reduces the potentially high plasma levels of the pharmacologically active idebenone. Because of this strong first pass metabolism, oral administration of idebenone requires high doses of the compound to achieve pharmacologically efficacious plasma levels in the body. Said high doses can result in unwanted side effects such as diarrhea.

In addition, the requirement for oral formulations of idebenone to be swallowed inflicts difficulties in the practical administration to patients with swallowing problems, e.g. a patient with a serious neuromuscular disease such as Duchenne Muscular Dystrophy or Friedreich's Ataxia, elderly or young patients.

SUMMARY OF ADVANTAGEOUS EMBODIMENTS OF THE INVENTION

A solution to this problem is presented in this invention which is based on data obtained with a specific type of transmucosal administration system consisting of especially a thin polymer-based film that when attached to the oral mucosa releases the active ingredient directly to the mucosa or partly into the saliva in the oral cavity, esophagus and stomach. The active ingredient is absorbed through the mucosa primarily in the oral cavity, esophagus and stomach, thus avoiding the first-pass metabolism observed after conventional oral administration and gastrointestinal absorption. This dosage form is also described as oral wafer.

The principle of this system is also applicable to analogues of idebenone, such as other benzoquinones or quinones, having a reversibly reducible quinone ring, with a lipophilic side chain. The term "ubiquinone analogues", as used herein, encompasses natural ubiquinones (coenzyme Q-n) as well as their structural analogs having a reversibly reducible quinone ring with a lipophilic side chain, for example idebenone or decylubiquinone.

Said object has been achieved by the use of a preferably thin film formulation (oral wafer) containing especially idebenone. Surprisingly it has been shown (see FIGURE) that the plasma levels of idebenone after oromucosal administration of wafer A (containing 30 mg), wafer B (containing 15 mg as a solid solution) are significantly higher compared to oral administration (300 mg/kg as microemulsion) in the same Beagle dogs (n=3).

BRIEF DESCRIPTION OF THE DRAWINGS

FIG. 1 is a graphical illustration of the mean plasma concentrations versus time of free idebenone after single administrations of various exemplary formulations (oral and thin wafer) in female Beagle dogs.

DETAILED DESCRIPTION OF ADVANTAGEOUS EMBODIMENTS OF THE INVENTION

The present invention relates to a transmucosal formulation, which comprises an effective amount of an active ingredient of the general structural formula (I) wherein $R^1$ is a lower alkyl group; $R^2$ is a hydrogen atom or an alkyl or alkenyl group which may be substituted; $R^3$ and $R^4$ each independently means a lower alkyl or lower alkoxy group or, taken together, mean a butadienylene group.

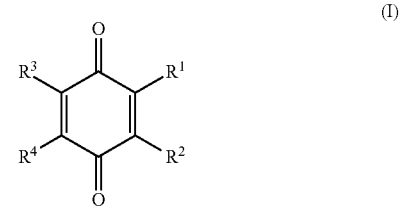

(I)

Referring to the above general formula (I), the lower alkyl group $R^1$ is a lower alkyl group of 1 to 4 carbon atoms, such as methyl, ethyl, propyl, butyl and so on. The alkyl moiety of the unsubstituted or substituted alkyl group $R^2$ includes acyclic hydrocarbon residues of 1 to 22 carbon atoms, such as methyl, ethyl, propyl, butyl, pentyl, hexyl, heptyl, octyl, nonyl, decyl, undecyl, dodecyl, tridecyl, pentadecyl, heptadecyl, eicosyl, docosyl and so on. Among them, an alkyl having 8 to 13 carbon atoms is preferable.

The alkenyl moiety of the unsubstituted or substituted alkenyl group $R^2$ include acyclic hydrocarbon residues of 2 to 15 carbon atoms, such as ethenyl, 1-propenyl, 3-methyl-2-butenyl, 3,7-dimethyl-2,6-octadienyl, etc., wherein the number of double bonds may generally range from 1 to 3 and these double bonds may be conjugated. Examples of substituents on the alkyl and alkenyl groups $R^2$ include hydroxy, carboxy, alkoxycarbonyl (e.g. C1-4 alkoxycarbonyl groups such as methoxycarbonyl, ethoxycarbonyl, propionyloxycarbonyl, butoxycarbonyl, etc.), aryl (e.g. phenyl, 1-naphthyl, 2-naphthyl, indanyl, etc.), heterocyclic groups (e.g. 2-pyridyl, 3-pyridyl, 2-thienyl, 3-thienyl, etc.) and halogen (e.g. fluorine, chlorine, bromine and iodine). Where the substituent group is such an aryl group or a heterocyclic group, the group may be nuclearly substituted by one or more substituents in optional positions of the ring structure. The substituents mentioned just above include, but are not limited to, unsubstituted C1-4 alkyl groups (e.g. methyl, ethyl, propyl, butyl, etc.), hydroxy, carboxy, and C2-5 alkoxycarbonyl (e.g. methoxycarbonyl, ethoxycarbonyl, propoxycarbonyl, butoxycarbonyl, etc.). The position of substitution on the alkyl or alkenyl group $R^2$ is optional but preferably 1-position or .omega.-position. The lower alkyl group, represented by $R^3$ and $R^4$, may be a C1-6 alkyl group, such as methyl, ethyl, propyl, i-propyl, butyl, i-butyl, sec-butyl, t-butyl, amyl, hexyl, etc. and preferably a C1-3 alkyl group. These lower alkyl groups may have substituents such as hydroxy, halogen (fluorine, chlorine, bromine and iodine), nitro, trifluoromethyl, carboxy, C2-5 alkoxycarbonyl (e.g. methoxycarbonyl, ethoxycarbonyl, etc.), 3-pyridyl, 1-imidazolyl, 5-thiazolyl and so on. The lower alkoxy group, represented by $R^3$ and $R^4$, may be a C1-3 alkoxy group such as methoxy, ethoxy, propoxy, i-propoxy and so on. Where $R^3$ and $R^4$ mean a butadienylene group, they constitute a benzene ring in association with the carbon atoms to which $R^3$ and $R^4$ are respectively attached, and the benzene ring so constituted may have 1 to 3 substituent groups in optional positions, which substituent groups include, among others, lower (C1-3) alkyl groups (e.g. methyl, ethyl, propyl, etc.), lower (C1-3) alkoxy groups (e.g. methoxy, ethoxy, propoxy, etc.), hydroxy, nitro and halogen.

The present invention relates also to the use of quinone or benzoquinone, especially idebenone (International Nonproprietary Name (INN): idebenone; Chemical name: 2-(10-Hydroxydecyl)-5,6-dimethoxy-3-methyl-2,5-cyclohexadiene-1,4-dione; Chemical Abstracts Service (CAS) registry number: 58186-27-9) and its analogues for the preparation of a preferably thin film formulation that when attached to the oral mucosa releases the active ingredient directly to the mucosa or partly into the saliva in the oral cavity (also called oral wafer) and is used for transmucosal administration to human beings or animals. This type of system results in much higher plasma levels of the compound compared to the oral route of administration. The preferred transmucosal administration system for a pharmaceutical active ingredient as thin film (oral wafer) formulations comprising as an active ingredient idebenone together with additives and excipients in conjunction with an appropriate manufacturing process used for this type of formulations are further described herein.

Idebenone has the following chemical structural formula (II):

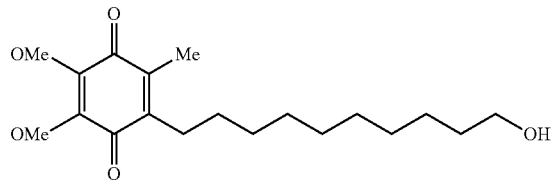 [SMILES: COC1=C(OC)C(=O)C(CCCCCCCCCCO)=C(C)C1=O]

2,3-dimethoxy-5-methyl-6-(10-hydroxydecyl)-1,4-benzoquinone, idebenone

Idebenone, a member of the quinone family, has been promoted commercially as a synthetic analog of Coenzyme Q10, and has been indicated to be suitable for treating a number of diseases and/or conditions. Moreover, it has been made the subject of various medical studies investigating its efficacy in the treatment of, for example, neuromuscular diseases such as Friedreich's Ataxia or neurological diseases such as Alzheimer's disease. Idebenone has also been used in topical applications to treat wrinkles. Therefore, idebenone may be regarded as toxicologically safe which means that it can be used as a pharmaceutical active agent in a medication. The toxicological safety of Idebenone has been confirmed in a clinical study with 536 patients that have been treated with up to 360 mg of idebenone t.i.d. (ter in die). Compared to the placebo treated control group, no treatment emergent adverse events except some gastrointestinal irritations as well as a slight increase in orthopedic events were observed (L. J. Thal, M. Grundman, J. Berg, K. Ernstrom, R. Margolin, E. Pfeiffer, M. F. Weiner, E. Zamrini, R. G. Thomas, *Neurology* 61 (2003), 1498-1502).

It has now been observed that, after conventional oral administration and absorption in the gut, idebenone is rapidly metabolized during its first passage through the liver. The major metabolites are idebenone conjugates such as glucuronates and sulphates as well as derivatives where the side chain of the parent compound has been oxidized. The metabolites of idebenone are pharmacologically not significantly active and they are rapidly excreted. Due to this strong first pass metabolism, oral administration of idebenone requires high doses in order to reach pharmacologically active plasma levels. These high doses result in unwanted effects such as diarrhea and gastrointestinal (GI) tract disturbances which are frequently observed in clinical applications.

Using the preferred thin film formulation (oral wafer) it has surprisingly been found that even with a 20-fold lower dose compared to the oral administration route, a more than 5-fold AUC can be achieved which, on a dose-normalized level, leads to a >100-fold AUC (see Table 4). Moreover, this opens up possibilities to achieve plasma levels of the pharmacologically active molecule that are far above those achievable via the oral route of administration.

By use of this system and the transmucosal route of administration, the high first pass metabolism observed after conventional oral administration of idebenone can very effectively be circumvented.

Circumvention of the strong first-pass metabolism of idebenone by using the thin film formulation (oral wafer) enables;

a) similarly high plasma levels of this active ingredient to be obtained whilst significantly reducing the dose that has to be administered. Lower active ingredient exposure is generally believed to be associated with a reduced risk of adverse side effects and offers a medical advantage leading to improved compliance by the patient. In the particular case of idebenone, the described GI side effects that can be avoided.
b) significantly higher plasma levels compared to those achievable with an oral formulation of the active ingredient being absorbed via the gastrointestinal route. This may lead to extension of the use of idebenone to additional, new indications in the field of neuromuscular diseases that require high concentrations e.g. in order to cross the blood-brain-barrier.
c) increased patient convenience as the film formulation (oral wafer) is thin, easy to handle and one unit is able to replace swallowing of several large tablets.
d) administration of a thin film formulation (oral wafer) to patients with swallowing difficulties, such as patients suffering from certain neuromuscular diseases or children below the age of 8, could increase compliance and convenience of use.

In the present invention, "thin film formulations" or "oral wafer" means a formulation that is intended to be applied and/or administered to the oral mucosa of a patient and where the active ingredient is absorbed into the body through the mucosa. According to the invention, such formulation constitutes the basis of medication containing idebenone for this specific route of administration. The oral mucosa comprise the mucosa in the entire oral and connecting cavities including but not limited to the sublingual, buccal, gingival, lingual, as well as the esophageal mucosa. The system has preferably a monolayer or double-layer construction.

The objective upon which the present invention is based is achieved through an transmucosal administration system which dissolves in the mouth of a patient and which comprises 0.01 to 80% by weight, preferably 2-70% by weight, of at least one quinone and 20-99.99% by weight, preferably 30-98% by weight, of a carrier material. Suitable carrier materials are in particular cellulose and derivatives thereof such as methylcellulose, ethylcellulose, hydroxypropyl-cellulose, hydroxyethylcellulose, hydroxypropylmethyl-cellulose (HPMC), carboxymethylcellulose (CMC); poly-alcohols such as poly-vinyl-alcohol (PVA); poly-N-vinylpyrrolidones; vinyl-pyrrolidone-vinyl acetate copolymers; starch; starch derivatives; gelatin; gelatin derivatives; SOLUPLUS® (a polyvinyl caprolactam-polyvinyl acetate-polyethylene glycol graft copolymer); KOLLICOAT® (a polyvinyl alcohol-polyethylene glycol graft copolymer) and combinations thereof. The administration system releases the quinone contained therein with a high bioavailability. Preferably, the system will be able to achieve high bioavailability without the addition of permeation enhancers.

An administration system containing a suspension of the active ingredient would preferably comprise 30-60% by weight, particularly preferably 40-50% by weight, of a quinone—especially of an 1,4-benzoquinone—and 40-70% by weight of a carrier material—especially a poly-alcohol and/or a cellulose derivative wherein the active ingredient is preferably micronized. Micronisation involves the reduction of particles to a size of preferably less than 100 µm, particularly preferably less than 10 µm.

An administration system containing an amorphous presentation (or amorphous composition) of the active ingredient would preferably comprise 3-20% by weight, particularly preferably 5-10% by weight of a quinone—especially of a 1,4-benzoquinone—and 80-97% by weight of a carrier material—especially a suitably substituted carbohydrate or other water soluble polymer.

An administration system containing an emulsion of the active ingredient would preferably comprise 3-50% by weight, particularly preferably 5-30% by weight of a quinone—especially of a 1,4-benzoquinone—and 50-97% by weight of a carrier material—especially a cellulose derivative.

One particularly preferred administration system comprises 50% by weight of a 1,4-benzoquinone of the group consisting of idebenone, idebenone analogues, ubiquinone, or ubiquinone analogues and 40% by weight of poly-vinyl alcohol (PVA) and 10% by weight of sodium carboxymethyl-cellulose carrier material.

Another particularly preferred administration system comprises 10% by weight of a 1,4-benzoquinone of the group consisting of idebenone, idebenone analouges, ubiquinone, or ubiquinone analouges and 90% by weight of HPMC carrier material.

It is preferred for the present invention that the administration systems which dissolves in the mouth to be in film form. These administration systems in film form are also referred to as "strips" or "wafers". The inventive administration systems in film form can, in a particular embodiment, be designed such that it has mucoadhesion. By this, it is meant that the property of adhering to a mucous membrane of a patient, specifically in such a manner that it is difficult or impossible to detach the administration system from the mucous membrane subsequent to the application.

For the present invention, it is preferred that the film administration system have a high surface area to weight ratio. It is also preferred that the administration system is in or forms a gel-like consistency in the oral cavity upon swelling in saliva.

The administration systems in film form of the present invention have an area of between 1 and 10 $cm^2$, preferably between 2 and 8 $cm^2$ and particularly preferably between 5 and 7 $cm^2$. They, moreover, have a weight per unit area between 50 and 250 $g/m^2$, preferably between 100 and 150 $g/m^2$. The latter approximately correlates with a thickness of between 40 and 300 µm, preferably between 50 and 100 µm.

The administration system dissolves in the mouth of a patient preferably in a period of less than 30 min, particularly preferably in a period of less than 15 min. The quinone which enters the bloodstream transmucosally from the administration system leads to a rapid rise in the concentration of this quinone in the blood. In this case, a maximum concentration of the quinone in the blood is reached preferably in a period of less than 60 min—particularly preferably in a period of between 5 and 30 min—after application. It is possible with the administration system to achieve a relatively high bioavailability, as measured by the AUC of the active ingredient concentration in the blood, of at least a factor of 5 times (500%) greater, preferably of at least a factor of 10 (1000%) greater than that of the quinone in tablet form (or simulated tablet form), when adjusted for the dose administered. A particularly preferred increase in bioavailability would be a factor of 20 (2000%) greater.

The administration system in film form may, besides the carrier material and the quinone, comprise further substances, for example flavorings, colorants, sweeteners, fillers, plasticizers, surface-active substances, liquid—preferably lipophilic—excipients which are able to dissolve the quinone and form a second phase in the—preferably hydrophilic—carrier material, solubilizers, pH stabilizers, disintegrants, solubility enhancers, absorption enhancers, and or permeation enhancers.

Quinones according to the present invention may be 1,4-hydroquinones and related compounds. The preferred 1,4-hydroquinones are idebenone, idebenone analouges, and ubiquinone and their related compounds. The term "ubiquinone and their related compounds", as used herein, encompasses natural ubiquinones (coenzyme Q-n) as well as their structural analogs having a reversibly reducible quinone ring with a lipophilic side chain.

The transmucosal administration system of 1,4-hydroquinones and related compounds according to the present invention can be used in the treatment of patients suffereing from various diseases and/or conditions, including mitochondrial, neuromuscular or neurological diseases. Examples of diseases to be treated include, but are not limited to, Friedreich's Ataxia, Duchenne Muscular Dystrophy, Becker Muscular Dystrophy, Alzheimer's Disease, Leber's Hereditary Optic Neuropathy, MELAS (mitochondrial myopathy, encephalopathy, lactic acidosis with stroke-like episodes), Parkinson's Disease and mitochondrial myopathies. In addition, there is preliminary evidence that the 1,4-benzoquinone, Coenzym Q10 or CoQ10, may be effective in treating coronary heart disease, Myoclonic epilepsy and ragged-red fibers, Kearns-Sayre syndrome, progressive external ophthalmoplegia, Diabetes mellitus and deafness, Leigh syndrome, subacute sclerosing encephalopathy, NARP (Neuropathy, ataxia, retinitis pigmentosa, and ptosis), and Myoneurogenic gastrointestinal encephalopathy, migraines, cancer, hypertension, age-related macular degeneration, Alzheimer's disease, Anthracycline chemotherapy heart toxicity, asthma and many others. Another particular application is the co-administration of 1,4-benzoquinone with statins and beta blockers to patients.

Compared to the efficacious dose of idebenone administered via the conventional oral route of administration and absorption in the gastrointestinal tract the efficacious dose of the formulation described in this application is expected to be significantly lower. On the other hand, it is expected that with this formulation and depending on the actual dose applied, significantly higher plasma levels and potentially increased clinical efficacy may be achievable within patients. Moreover, due to the higher plasma levels the use of idebenone can be extended to additional indications in the field of neuromuscular diseases that require high concentrations of drug substance e.g. in order to cross the blood-brain-barrier within patients.

Suitable doses of the active ingredient administered by thin film formulation (oral wafer) are 0.01 mg/kg/day to 60 mg/kg/day. Preferably, for example idebenone is administered in a dosage of 0.01 mg/kg/day to 20 mg/kg/day, more preferably in a dosage of 0.01 mg/kg/day to 10 mg/kg/day and even more preferably in a dosage of 0.01 mg/kg/day to less than 5 mg/kg/day. Most preferably, the dosage of the active ingredient idebenone is between 0.1 mg/kg/day to 4 mg/kg/day. Studies have shown that, surprisingly, such low dosages achieve the required plasma level of idebenone if it is applied via the oral mucosa. The required dosage may be ascertained readily by a person skilled in the art.

In a preferred embodiment, idebenone may be administered in combination with a second therapeutic agent, wherein said second therapeutic agent is preferably selected from glucocorticosteroids such as 6a-methylprednisolone-21 sodium succinate (SOLUMEDROL®) or deflazacort (CALCORT®) which are routinely used in DMD patients for treatment of inflammation and muscle weakness. Likewise, idebenone may be administered in combination with any medicament used in DMD patients to treat DMD-associated cardiomyopathy such as ACE-inhibitors, beta-blockers and diuretics as well as HMG-CoA reductase inhibitors.

In a further preferred embodiment, idebenone may be administered in combination with further therapeutic agents, wherein said further therapeutic agents are preferably erythropoietin, vitamin E, vitamin C, or mitoquinone (MitoQ; K. M. Taylor, R. Smith, WO05019232A1).

Idebenone and other therapeutic agents can be used simultaneously, separately or sequentially in order to treat or prevent the disease symptoms. The therapeutic agents may be provided in a single dosage form or as separate formulations, each formulation containing at least one of the active agents.

The following examples illustrate the invention, but are not intended to limit the scope of the invention.

Example 1

112 g of PVA is added to 720 mL of water and stirred until dissolution is complete. The dissolution is assisted where appropriate by application of heat. After cooling, 140 g of idebenone is dispersed uniformly. Afterward, 28 g of CMC is added, and the mixture is stirred until dissolution is complete.

The mixture is degassed, coated and dried. A thin opaque film which is between 50 and 150 µm thick is produced. Opaque wafers with a content of 30 mg of idebenone are obtained by cutting out samples of the appropriate size.

Example 2

28 g of idebenone are added to 720 mL of 75:25 methanol:water, which is stirred until the active ingredient has completely dissolved. 250 g of HPMC are added and stirred until dissolution is complete. Degassing of the mixture and coating are followed by drying. A thin translucent film which is between 100 and 300 µm thick is produced. Translucent wafers with a content of 15 mg of idebenone are obtained by cutting out samples of the appropriate size.

It may be noted that the dried systems of example 1 comprise the benzoquinone as particles in a separate phase suspended in the carrier material, whereas the benzoquinone in examples 2 is in the form of a mono-molecular dispersion in the carrier material.

Experimental Data:
Pharmacokinetic Data after Oromucosal Delivery of Idebenone

Plasma levels of idebenone were studied after the administration of two different thin film formulations (oral wafers) administered via the oromucosal route and compared to the profile obtained when idebenone is dosed by the oral route (gavage) in a micro-emulsion. The doses used in this study were 30 mg oromucosal (oral wafer A, suspension type), 15 mg oromucosal (oral wafer B, solid solution type) and 300 mg oral (TPGS/Miglyol microemulsion administered by oral gavage). The study was a three way cross-over study with one week wash-out between administrations. Formulations were administered to female Beagle dogs under fasted conditions. The pharmacokinetic exposure of free (unconjugated) idebenone and its total metabolites (total idebenone, total QS10, total QS6, and total QS4) was determined for each formulation.

Blood samples were collected at several time points over 6 hours after administration. Concentrations of idebenone in plasma were measured by HPLC-MS/MS and pharmacokinetic parameters were calculated.

For this, idebenone was separated and quantified by HPLC-MS/MS: For HPLC, a SYNERGI™ 4μ MAX-RP (50×2 mm) column (Phenomenex, Schlieren, Switzerland) was used. Column temperature: 50° C. Mobile phase A: water +30 mM NH$_4$OAc; mobile phase B: MeOH/H$_2$O 100/3 (v/v)+30 mM NH$_4$OAc, gradient elution (table 4). Flow: 250 μl/min and 400 μl/min.

Once separated, idebenone was quantified by ESI-MS/MS (API 4000, Perkin-Elmer-Europe BV, Rotkreuz, Switzerland) in positive mode.

TABLE 1

Pump-gradient program and time events for separation and quantification of idebenone

| Time [min] | mobile phase B [%] | Flow [μl/min] | Comments |
|---|---|---|---|
| 0.01 | 50 | 250 | start gradient, HPLC eluent to MS |
| 3.00 | — | 250 | — |
| 3.01 | — | 400 | — |
| 3.75 | 95 | 400 | end gradient |
| 4.50 | 95 | 400 | — |
| 4.51 | 50 | 400 | — |
| 5.90 | 50 | 400 | — |
| 5.91 | 50 | 250 | — |
| 29.99 | 50 | 250 | pump shutdown |
| 30.00 | 95 | 20 | |

From times 0.01 to 3.75 min a linear gradient was used.

Idebenone conjugates such as glucuronates and sulphates have been quantified after acidic hydrolysis as described by R. Artuch, C. Colomé, M. A. Vilaseca, A. Aracil. M. Pineda, J. Neurosci. Meth. 115 (2002), 63-66.

The pharmacokinetic analysis included maximum plasma concentration ($C_{max}$), the time when maximum plasma concentration was observed ($T_{max}$), and the area under the plasma concentrations versus time curve from time 0 h to 360 min ($AUC_{0-360\ min}$). The relative bioavailability of idebenone after sublingual administration compared to the oral administration was calculated for each dog from normalized (1 mg/kg) AUC values. The AUC ratios of the metabolites were also calculated. In addition, $C_{max}$ ratios, normalized to a 1 mg/kg dose, were calculated.

The results obtained are shown in Table 2 to below.

TABLE 2

Mean pharmacokinetic parameters of idebenone after oromucosal (30 mg wafer A) and (15 mg wafer B) vs. oral (300 mg, microemulsion) administration in dogs.

| Dosing | $C_{max}$ [ng/ml] | $T_{max}$ [min] | $AUC_{0-360}$ [min*ng/ml] |
|---|---|---|---|
| 30 mg wafer A (micronized suspension) | 248 | 15 | 6152 |
| 15 mg wafer B (solid solution) | 404 | 25 | 13864 |
| 300 mg oral gavage (microemulsion) | 111 | 7 | 2305 |

As shown in Table 2, the two wafer formulations of idebenone administered via the oromucosal route, prepared according to example 1 and 2, clearly lead to significantly higher plasma levels of idebenone compared to conventional oral administration. Both $C_{max}$ and $AUC_{0-360}$ were superior to the oral administration in both thin film (oral wafer) formulations. There is also a marked difference between wafer A, which contains 30 mg idebenone as micronized powder suspended in the polymer matrix, and wafer B, which contains only 15 mg but in a solid solution, i.e. molecularly dispersed state. The latter clearly dissolves much more efficiently and is better absorbed.

FIG. 1 illustrates the mean plasma concentrations versus time of free idebenone after single administrations of various formulations (oral and thin wafer) in female Beagle dogs.

As shown in FIG. 1, wafer B (15 mg, solid solution type wafer) showed the highest $C_{max}$ and the largest AUC compared to the other treatment arms. Wafer A (30 mg, suspension type wafer) shows a higher $C_{max}$ and a larger AUC compared to the oral route (300 mg, microsuspension).

TABLE 3

Mean pharmacokinetic parameters of idebenone after oromucosal (30 mg wafer A) and (15 mg wafer B) vs. oral (300 mg, microemulsion) administration in dogs after dose normalization per mg.

| Dosing | $C_{max}$/mg [ng/ml] | $AUC_{0-360}$/mg [min*ng/ml] |
|---|---|---|
| 30 mg wafer A (micronized suspension) | 8.3 | 205 |
| 15 mg wafer B (solid solution) | 26.9 | 924 |
| 300 mg oral gavage (microemulsion) | 0.4 | 7.7 |

As shown in Table 3: above, the magnitude of increase in exposure obtained with the two wafer formulations of idebenone administered via the oromucosal route (prepared according to example 1 and 2) compared to the oral route of administration becomes even more apparent after normalization for differences in dose.

TABLE 4

Comparison of the mean pharmacokinetic parameters of the different formulations after dose normalization per mg.

| Dosing | $C_{max}$/mg [ng/ml] | $AUC_{0-360}$/mg [min*ng/ml] |
|---|---|---|
| Comparison wafer A vs. oral gavage | 33 | 26 |
| Comparison wafer B vs. oral gavage | 144 | 121 |
| Comparison wafer B vs. wafer A | 3.62 | 4.75 |

As shown in Table 4: The comparison on a dose-normalized basis shows that wafer A lead to a 26-fold higher AUC (33-fold $C_{max}$) than the oral formulation on a dose normalized level and wafer B lead to a 121-fold higher AUC (144-fold $C_{max}$) in comparison to the oral route. The solid solution wafer B leads to >4-fold higher exposure of idebenone compared to the suspension type wafer A.

In summary it can be concluded that

Oral-mucosal administration of idebenone by a thin film formulation (oral wafer) based on the solid-solution technology strongly improves the relative bioavailability of idebenone by approximately 100 fold over oral administration. The main reason for the increased bioavailability is the initial bypass of the enterohepatic circulation.

On top of that, there is evidence that the absorption of idebenone from this wafer is increased compared to an oral administration of idebenone by gavage.

A wafer, based on the micronized suspension technology, also improves the relative bioavailability of idebenone, though to a lesser extent The metabolic spectrum of idebenone is comparable after oral administration by gavage and the oral-mucosal application The oral wafer formulation offers the following advantages over the formulations administered via the oral route:

Significant dose reduction (less side effects)
Higher plasma levels achievable
Increased patient convenience
Administration to patients with swallowing difficulties The inventive systems may further comprise a polymer matrix and the pharmaceutical active ingredient may be incorporated within the polymer matrix as a suspension, a suspension after micronization, an emulsion, a micro- or nano-emulsion, or in solubilised and/or molecularly dispersed form.

That which is claimed:

1. A transmuccosal administration system comprising pharmaceutical ingredient consisting of active ingredient selected from the group consisting of idebenone, idebenone analogues, decylubiquinone, ubiquinone and ubiquinone analogues and 80 to 97% by weight of a carrier material and optional second or further therapeutic agents, wherein said administration system is a film having a weight per unit area of between 50 and 250 g/m$^2$ and said pharmaceutical ingredient is present in an amount ranging from 3 to 20% by weight, said pharmaceutical ingredient is molecularly dispersed within said carrier material, said system either has a gel consistency or forms a gel consistency upon swelling in saliva, and the system exhibits an AUC of the active ingredient concentration in the blood that is at least 100-fold greater than that exhibited through administering the active ingredient through the oral route on a dose-normalized basis.

2. The administration system as claimed in claim 1, wherein the carrier material is selected from the group consisting of cellulose, cellulose derivatives, polyvinyl-alcohol, poly-N-vinylpyrrolidones, vinylpyrrolidone-vinyl acetate copolymers, starch, starch derivatives, gelatine, gelatine derivatives, polyvinyl caprolactam-polyvinyl acetate-polyethylene glycol graft copolymer, polyvinyl alcohol-polyethylene glycol graft copolymer, and combinations thereof.

3. The administration system as claimed in claim 2, wherein the cellulose derivate is methylcellulose, ethylcellulose, hydroxypropylcellulose, hydroxyethylcellulose, hydroxypropylmethylcellulose, carboxymethylcellulose or combinations thereof.

4. The administration system as claimed in claim 1, wherein said system comprises 50% by weight of a 1,4-benzoquinone as active ingredient selected from the group consisting of idebenone, ubiquinone or ubiquinone analogues and 40% by weight polyvinyl alcohol and 10% by weight of sodium carboxymethyl-cellulose as carrier material.

5. The administration system as claimed in claim 1, wherein said system comprises 10% by weight of a 1,4-benzoquinone as active ingredient selected from the group consisting of idebenone, ubiquinone or ubiquinone analogues and 90% by weight of hydroxypropylmethylcellulose as carrier material.

6. The administration system as claimed in claim 1, wherein a maximum concentration of the active ingredient in the blood is reached in a period of less than 240 minutes after application.

7. The administration system as claimed in claim 6, wherein a maximum concentration of the active ingredient in the blood is reached in a period of less than 60 minutes after application.

8. The administration system as claimed in claim 6, wherein a maximum concentration of the active ingredient in the blood is reached in a period of between 5 and 30 min after application.

9. The administration system as claimed in claim 1, wherein the system additionally comprises excipient consisting of at least one of flavorings, colorants, sweeteners, fillers, plasticizers, surface-active substances, solubilizers, liquid excipient, pH stabilizers, disintegrants, solubility enhancers and absorption enhancers.

10. The administration system as claimed in claim 1, wherein the active ingredient is present dissolved in the carrier material and/or a liquid excipient.

11. The administration system as claimed in claim 10, wherein the liquid excipient is a liquid lipophilic excipient.

12. The administration system as claimed in claim 1, wherein the system has an area of between 1 and 10 cm$^2$.

13. The administration system as claimed in claim 1, wherein the system has an area of between 2 and 8 cm$^2$.

14. The administration system as claimed in claim 1, wherein the system has an area of between 5 and 7 cm$^2$.

15. The administration system as claimed in claim 1, wherein system has a weight per unit area of between 100 and 150 g/m$^2$.

16. The administration system as claimed in claim 1, wherein the system has a thickness of between 40 and 300 μm.

17. The administration system as claimed in claim 1, wherein the system has a thickness of between 50 and 100 μm.

18. The administration system as claimed in claim 1, wherein the active ingredient is micronized.

19. The administration system as claimed in claim 1, wherein the system contains 5-10% by weight of the active ingredient and 80-97% by weight of a water soluble polymer as carrier material.

20. The administration system as claimed in claim 1, wherein the system contains an emulsion comprising 3-50% by weight of the active ingredient and 50-97% by weight of a cellulose derivate as carrier material.

21. The administration system as claimed in claim 1, wherein the system contains an emulsion comprising 5-30% by weight of the active ingredient and 50-97% by weight of a cellulose derivate as carrier material.

22. The administration system as claimed in claim 1, wherein the system has a monolayer or double-layer construction.

23. The administration system as claimed in claim 1, wherein said system consists of said pharmaceutical ingredient, carrier material and optional second or further therapeutic agents consisting of glucocorticosteroids, ACE-inhibitors, beta-blockers, diuretics, HMG-CoA reductase inhibitors, erythropoietin, vitamin E, vitamin C or mitoquinone and optional excipient consisting of at least one of flavorings, colorants, sweeteners, fillers, plasticizers, surface-active substances, solubilizers, liquid excipient, pH stabilizers, disintegrants, solubility enhancers and absorption enhancers.

24. The administration system as claimed in claim 1, wherein said system comprises 10% by weight of said pharmaceutical ingredient.

25. A transmuccosal administration system comprising pharmaceutical ingredient consisting of active ingredient selected from the group consisting of idebenone, idebenone analogues, decylubiquinone, ubiquinone and ubiquinone analogues and 40 to 70% by weight of a carrier material and optional second or further therapeutic agents, wherein said administration system is a film having a weight per unit area of between 50 and 250 g/m$^2$ and said pharmaceutical ingredient is present as a suspension after micronization in an amount ranging from 30 to 60% by weight; and the system is a mucoadhesive film which dissolves in the mouth, the active ingredient is micronized into particles of less than 100 microns and absorbed through the mucosa primarily in the oral cavity, esophagus and stomach; and the system results in a higher plasma level of active ingredient than imparted by oral administration dosage forms absorbed in the gastrointestinal tract and the system exhibits an AUC of the active ingredient concentration in the blood that is at least 20 fold greater than that exhibited through administering the active ingredient through the oral route on a dose-normalized basis.

26. The administration system as claimed in claim 25, wherein the film dissolves completely in a period of less than 30 minutes in the mouth.

27. The administration system as claimed in claim 25, wherein the film dissolves completely in a period of less than 15 minutes in the mouth.

28. The administration system as claimed in claim 25, wherein the system contains a suspension comprising 40-50% by weight of the active ingredient and 40-70% by weight of a polyalcohol and/or a cellulose derivate as carrier material.

29. The administration system as claimed in claim 25, wherein said carrier material is selected from the group consisting of cellulose, cellulose derivatives, polyvinyl-alcohol, poly-N-vinylpyrrolidones, vinylpyrrolidone-vinyl acetate copolymers, starch, starch derivatives, gelatine, gelatine derivatives, polyvinyl caprolactam-polyvinyl acetate-polyethylene glycol graft copolymer, polyvinyl alcohol-polyethylene glycol graft copolymer, and combinations thereof.

30. The administration system as claimed in claim 29, wherein said carrier material comprises 40% by weight of said poly-vinyl alcohol and 10% by weight of cellulose derivatives.

31. A treatment method comprising administering to a patient suffering from a disease and/or condition a dose of the system as claimed in claim 1 in an amount of equal to or less than 60 mg/kg/day.

32. The treatment method as claimed in claim 31, wherein the disease is disease caused by mitochondrial dysfunction, neurological diseases and/or neuromuscular diseases.

33. The treatment method as claimed in claim 31, wherein the disease and/or condition is Friedreich's Ataxia (FRDA), Leber's Hereditary Optic Neuropathy (LHON), mitochondrial myopathy, encephalopathy, lactic acidosis with stroke-like episodes (MELAS) and/or mitochondrial myopathies.

34. The treatment method as claimed in claim 31, wherein the disease and/or condition is Duchenne Muscular Dystrophy and/or Becker Muscular Dystrophy.

35. The treatment method as claimed in claim 31, wherein the disease and/or condition is Alzheimer's disease and/or Parkinson's disease.

36. The treatment method as claimed in claim 31, wherein the pharmaceutical active ingredient is idebenone and the idebenone is administered in a dosage from 0.01 mg/kg/day to 10 mg/kg/day.

37. The treatment method as claimed in claim 31, wherein the pharmaceutical active ingredient is idebenone and the system further comprises a polymer matrix wherein the idebenone is incorporated within the matrix as a suspension, a suspension after micronization, an emulsion, a micro- or nano-emulsion, or in solubilised and/or molecularly dispersed form.

38. The treatment method as claimed in claim 31, wherein the administering step comprising administering a dosage via the oral mucosa on or under the tongue in the buccal cavity or any other location in the oral cavity.

39. The treatment method as claimed in claim 31, wherein said method further comprises administering a second therapeutic agent.

\* \* \* \* \*